US006949515B2

(12) United States Patent
Demuth et al.

(10) Patent No.: US 6,949,515 B2
(45) Date of Patent: Sep. 27, 2005

(54) EFFECTORS OF DIPEPTIDYL PEPTIDASE IV FOR TOPICAL USE

(75) Inventors: Hans-Ulrich Demuth, Halle/Saale (DE); Torsten Hoffmann, Halle/Saale (DE); Dagmar Schlenzig, Halle/Saale (DE); Ulrich Heiser, Halle/Saale (DE)

(73) Assignee: Probiodrug AG, Halle/Saale (DE)

( * ) Notice: Subject to any disclaimer, the term of this patent is extended or adjusted under 35 U.S.C. 154(b) by 160 days.

(21) Appl. No.: 10/082,001

(22) Filed: Feb. 22, 2002

(65) Prior Publication Data

US 2003/0092630 A1 May 15, 2003

Related U.S. Application Data

(63) Continuation of application No. PCT/EP00/08118, filed on Aug. 20, 2000.

(30) Foreign Application Priority Data

Aug. 24, 1999 (DE) .......................................... 199 40 130

(51) Int. Cl.⁷ .......................... A61K 38/00; A61K 31/33
(52) U.S. Cl. ...................... 514/19; 514/183; 424/94.63; 424/78.02; 544/141; 548/200; 548/400; 548/535
(58) Field of Search ................ 514/19, 183; 424/94.63, 424/78.02; 544/141; 548/200, 400, 535

(56) References Cited

U.S. PATENT DOCUMENTS

| | | | |
|---|---|---|---|
| 2,961,377 A | 11/1960 | Shapiro et al. | 167/65 |
| 3,174,901 A | 3/1965 | Sterne | 167/65 |
| 3,879,541 A | 4/1975 | Kabbe et al. | 424/326 |
| 3,960,949 A | 6/1976 | Ahrens et al. | 260/564 B |
| 4,028,402 A | 6/1977 | Fischer et al. | 260/501.14 |
| 4,935,493 A | 6/1990 | Bachovchin et al. | 530/331 |
| 5,433,955 A | 7/1995 | Bredehorst et al. | 424/94.3 |
| 5,462,928 A | 10/1995 | Bachovchin et al. | 514/19 |
| 5,512,549 A | 4/1996 | Chen et al. | 514/12 |
| 5,543,396 A | 8/1996 | Powers et al. | 514/19 |
| 5,614,379 A | 3/1997 | MacKellar | 435/68.1 |
| 5,624,894 A | 4/1997 | Bodor | 514/2 |
| 5,705,483 A | 1/1998 | Galloway et al. | 514/12 |
| 5,827,898 A | 10/1998 | Khandwala et al. | 514/734 |
| 5,939,560 A | 8/1999 | Jenkins et al. | 548/535 |
| 6,006,753 A | 12/1999 | Efendic | 128/898 |
| 6,011,155 A | 1/2000 | Villhauer | 544/333 |
| 6,107,317 A | 8/2000 | Villhauer | 514/365 |
| 6,110,949 A | 8/2000 | Villhauer | 514/365 |
| 6,124,305 A | 9/2000 | Villhauer | 514/272 |
| 6,166,063 A * | 12/2000 | Villhauer | 514/423 |
| 6,172,081 B1 | 1/2001 | Damon | 514/307 |
| 6,201,132 B1 | 3/2001 | Jenkins et al. | 548/535 |
| 6,303,661 B1 | 10/2001 | Demuth et al. | 514/866 |
| 6,319,893 B1 | 11/2001 | Demuth et al. | 514/2 |
| 6,500,804 B2 | 12/2002 | Demuth et al. | 514/19 |
| 6,517,824 B1 * | 2/2003 | Kohn et al. | 424/78.06 |
| 6,548,481 B1 | 4/2003 | Demuth et al. | 514/19 |

FOREIGN PATENT DOCUMENTS

| | | |
|---|---|---|
| DE | 296 075 A5 | 11/1991 |
| DE | 196 16 486 C2 | 10/1997 |
| EP | 0 658 568 A1 | 6/1995 |
| EP | 0 708 179 A2 | 4/1996 |
| EP | 1 130 022 A1 | 9/2001 |
| JP | 04-288098 | 10/1992 |
| JP | 4334357 | 11/1992 |
| WO | WO 91/11457 | 8/1991 |
| WO | WO 91/16339 | 10/1991 |
| WO | WO 91/17767 | 11/1991 |
| WO | WO 93/08259 | 4/1993 |
| WO | WO 95/11689 | 5/1995 |
| WO | WO 95/15309 | 6/1995 |
| WO | WO 95/29691 | 11/1995 |
| WO | WO 97/40832 | 11/1997 ......... A61K/31/425 |
| WO | WO 97/45117 | 12/1997 |

(Continued)

OTHER PUBLICATIONS

Bergmeier, Stephen C., *Tetrahedron*, Elsevier Science Ltd., "The Synthesis of Vicinal Amino Alcohols", vol. 56, No. 17, (2000), pp. 2561–2576.

(Continued)

Primary Examiner—Jon Weber
Assistant Examiner—Chih-Min Kam
(74) Attorney, Agent, or Firm—John C. Serio; Brown Rudnick Berlack Isreals LLP (57) ABSTRACT

The invention relates to compounds for topically influencing the activity of dipeptidyl peptidase of the general formula

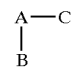

wherein
  A is an amino acid having at least one functional group in the side chain;
  B is a chemical compound covalently bound to a functional group of the side chain of A, chosen from the group consisting of
    (a) oligopeptides having a chain length of up to 20 amino acids,
    (b) homopolymers of glycine consisting of up to 6 glycine monomers, and
    (c) polyethylene glycols having molar masses of up to 20 000 g/mol; and
  C is a group amide-bonded to A chosen from the group consisting of thiazolidine, pyrrolidine, cyanopyrrolidine, hydroxyproline, dehydroproline or piperidine.

The invention further relates to the use of said compounds for targeted intervention in local immunological processes (chemotaxis, inflammatory processes, autoimmune diseases), as well as effective and targeted treatment of pathophysiological and physiological processes related thereto (psoriasis, periodontitis, arthritis, allergies, inflammation), inter alia.

19 Claims, 1 Drawing Sheet

FOREIGN PATENT DOCUMENTS

| WO | WO 98/19998 | 5/1998 | |
|----|----|----|----|
| WO | WO 98/22494 | 5/1998 | |
| WO | WO 99/46272 A | 9/1999 | |
| WO | WO 99/61431 | 12/1999 | |
| WO | WO 99/62914 | 12/1999 | |
| WO | WO 00/01849 | 1/2000 | |
| WO | WO 00/10549 | 3/2000 | |
| WO | WO 00/53171 | 9/2000 | ......... A61K/31/155 |
| WO | WO 01/09169 A2 | 2/2001 | |
| WO | WO 01/32624 A1 | 5/2001 | |
| WO | WO 01/34594 A1 | 5/2001 | |
| WO | WO 01/62266 A2 | 8/2001 | .......... A61K/38/00 |
| WO | WO 01/74299 A2 | 10/2001 | |
| WO | WO 01/89569 A1 | 11/2001 | |
| WO | WO 01/94310 A1 | 12/2001 | |
| WO | WO 01/97808 | 12/2001 | |
| WO | WO 02/20825 A1 | 3/2002 | |

OTHER PUBLICATIONS

Kawamoto et al., *Tetrahedron Asymmetry, Elsevier Science Ltd.,* "Anantioselective Synthesis of β–Hydroxy Amines and Aziridines Using Asymmetric Transfer Hydrogenation of α–Amido Ketones", vol. 11, No. 16 (2000), pp. 3257–3261.

Orskov, Cathrine et al., "Proglucagon Products in Plasma of Noninsulin–dependent Diabetics and Nondiabetic Controls in the Fasting State and after Oral Glucose and Intravenous Arginine"*J. Clin. Invest.,* vol. 87, 1991, pp. 415–423.

Reinhold, D. et al.,*Journal of Neuroimmunology,*"Inhibitors of Dipeptidyl Peptidase IV/CD26 Suppress Activation of Human MBP–Specific CD4+ T Cell Clones", (1998) 87:203–209.

Sengupta, et al., *Tetrahedron Letters, Elsevier Science Ltd.* "Amino Acid Derived Morpholine Amides for Nucleophilic α–Amino Acylation Reactions: A New Synthetic Route to Enantiopure α–Amino Ketones", vol. 40, No. 21 (1999), pp. 4107–4110.

Stöckel–Maschek, A., et al., *Biochimica et Biophysica Acta,* "Thioxo Amino Acid Pyrrolidides and Thiazolidides: new Inhibitors of Proline Specific Peptidases", (2000) 1479: 15–31.

Stryer, Lubert, *Biochemistry,* "Amino Acid Degradation and the Urea Cycle" (1975) pp. 451–452.

Mentlein et al., *Eur. J. Biochem,* Dipeptidyl–Peptidase IV Hydrolyses Gastric Inhibitory Polypeptide, Glucagon–Like Peptide–1(7,36)Amide, Peptide Histidine Methionine and is Responsible for Their Degradation in Human Serum. (1993), 214, pp. 829–835.

Campbell, I.W. *New Antidiabetic Drugs,* ed. C.J. Bailey & P.R. Flatt, Smith–Gordon, "Sulphonylureas and metformin: efficacy and inadequacy". 3:33–51 (1990).

The Merck Index, 11th Edition, *An Encyclopedia of Chemicals, Drugs,* and Biologicals, 1989, p. 934.

The Merck Index, 12th Edition, *An Encyclopedia of Chemicals, Drugs,* and Biologicals, 1996, p. 1014.

*Martindale The Extra Pharmacopoeia,* 30th Edition, London Pharmaceutical Press, 1993, p. 1619, p. 36.

*Chemical Abstracts,* vol. 115. No. 15, Oct. 14, 1991 Columbus, Ohio, US; abstract No. 149947q. Schoen Ekkehard et al: "Dipeptidyl peptidase IV in the immune system. Effects of specific enzyme inhibitors on activity of dipeptidyl peptidase IV and proliferation of human lymphocytes".

*Chemical Abstracts,* vol. 126, No. 2, Jan. 13, 1997 Columbus, Ohio, US; abstract No. 16161j, Stoeckel A. et al: "Competitive inhibition of proline specific enzymes by amino acid thioxopyrrolidides and thiazolidides".

*Chemical Abstracts,* vol. 118, No. 25, Jun. 21, 1993 Columbus, Ohio, US; abstract No. 255342k, Hosoda, et al, "Preparation of N–(heterocyclic Carbonyl) Amino Acids and Analogs and Prolyl Endopeptidase Inhibitors", Nov. 1992.

Arai et al., "Synthesis of prolyl endopeptidase inhibitors and evaluation of their structure–activity relationships : in vitro inhibition of prolyl endopeptidase from Canine Brain" *Chemical and Pharmaceutical Bulletin.,* Bd. 41, No. 9, 1993, pp. 1583–1588.

J. Lin et al.: "Inhibition of depeptidyl peptidase IV by fluorolefin–containing n–peptidyl–O–hydroxylamine peptidomimetics" *Proceedings of the National Academy of Sciences of USA,* vol. 95, Nov. 1998, pp. 14020–14024.

Korom, S., et al "Inhibition of CD26/dipeptidyl peptidase IV activity in vivo prolongs cardiac allograft survival in rat recipients", *Transplantation,* vol. 63, 1495–1500 (Nov. 10 (1997).

Tanka, S., et al., "Suppression of arthritis by the inhibitors of dipeptidyl peptidase IV", *Int. J. Immunopharmacol,* vol. 19, No. 1 pp. 15–24, (1997).

Mentlein, R., et al., "Proteolytic processing of neuropeptide Y and peptide YY by dipeptidyl peptidase IV". *Regul. Pept.* 49, 133–144 (1993).

Wetzel, W., et al., "Effects of the CLIP fragment ACTH 20–24 on the duration of REM sleep episodes". *Neuropeptides,* 31, 41–45 (1997).

Amasheh, S., et al., "Electrophysiological analysis of the function of the mammalian renal peptide transporter expressed in *Xenopus Laevis* oocytes". *J. Physiol.* 504, 169–174 (1997).

Durinx, C.; et al.; "Reference Values for Plasma Dipepidyl–Pepidase IV activity and their Association with Other Laboratory Parameters". *Clin Chem Lab Med 2001,* Feb.; 39 (2) :155–9, 1 page.

Gossrau, R.; "Cytochemistry of Membrane Proteases", *Histochem J,* Jul. 1985; 17 (7) :737–71, 1 page.

Hahn, T.; et al.; "Enzyme Histochemical Evidence for the Presence of Potential Blood Pressure Regulating Proteases in Cultured Villous Explants from Humans First Trimester Placentae". *Acta Histochem* Dec. 1993, 95 (2):185–92, 1 page.

Heymann, E. et al., "Has Dipeptidyl Peptidase IV an Effect on Blood Pressure and Coagulation." *Klin Wochenschr,* Jan., 2, 1984;62 (1) :2–10, 1 page.

Magyar, C.E. et al., "Proximal Tubule Na Transporter Responses are the same during Acute and Chronic Hypertension." *Am J. Physiol Renal Physiol,* Aug. 2000; 279 (2) :F358–69, 1 page.

Papies, B. et al., "Isoenzyme (Lactate Dehydrogenase, Asparatate Aminotransferase) and Dipeptidyl Peptidase IV Activity Changes in Blood Plasma Likely Indicative of Organ Involvement due to Arterial Hypertension." *Cor Vasa,* 1991; 33(3) :218–26, 1 page.

Qureshi. N.U.; et al., "Endogenous Neuropeptide Y Mediates Vasoconstriction during Endotoxic and Hemorrhagic Shock". *Regul Pept,* Sep. 25, 1998; 75–76:215–20, 1 page.

Index Nominum, *International Drug Directory 1992/1993,* Medpharm Scientific Publishers, pp. 728–729.

The Merck Index, *An Encyclopedia of Chemicals and Drugs,* 9th Edition, Merck & Co., Inc., 1976, p. 773.

Willms et al., *Journal of Clinical Endocrinology Metabolism*, "Gastric Emptying, Glucose Responses, and Insulin Secretion after a Liquid Test Meal: Effects of Exogenous Glucagon–Like Peptide–1 (GLP–1)–(7–36) Amide in Type 2 (Noninsulin–Dependent) Diabetic Patients", 1996, 81(1):327–332.

Hoffmann et al., *Journal of Chromatography A*, "Inhibition of dipeptidyl peptidase IV (DP IV) by anti–DP IV antibodies and non–substrate X–X–Pro– oligopeptides ascertained by capillary eletrophoresis", 1995, 716:355–362.

C.B. Welch, *Medical Management of Non–Insulin–Dependent (Type II) Diabetes*, $3^{rd}$ edition, American Diabetes Association, "Diagnosis and Classification" p. 3, 1994, Pharmacologic Intervention (2 pages).

Mannucci et al., *Diabetes Care*, "Effect of Metformin on Glucagon–Like Peptide 1 (GLP–1) and Leptin Levels in Obese Nondiabetic Subjects", 24(3): 489–494, Mar. 2001.

Stryer, *Biochemistry $3^{rd}$ Ed.*, "Protein Conformation, Dynamics, and Function", 1988, p 191–193.

Pauly et al., *Regulatory Peptides*, "Abstracts Issue: Abstracts from the $11^{th}$ International Symposium on Regulatory Peptides", Jul. 15, 1996, 64(1–3): 148 plus cover.

Gutniak et al., *New England Journal of Medicine*, "Antidiabetogenic Effect of Glucagon–like peptide–1 (7–36) Amide in Normal Subjects and Patients With Diabetes Mellitus", 1992, 326: 1316–1322.

Hendrick et al., *Metabolism—Clinical and Experimental*, "Glucagon–like Peptide–I–(7–37) Suppresses Hyperglycemia in Rats", Jan. 1993, 42(1): 1–6.

Nauck et al., *Diabetologia*, "Normalization of fasting hyperglycaemia by exogenous glucagon–like peptide 1 (7–36 amide) in Type 2 (non–insulin–dependent) diabetic patients", (1993), 36: 741–744.

Gutniak et al., *Diabetes Care*, "Subcutaneous Injection of the Incretin Hormone Glucagon–Like Peptide 1 Abolishes Postprandial Glycemia in NIDDM", Sep. 1994, 17(9): 1039–1044.

Deacon et al., *Journal of Clinical Endocrinology and Metabolism*, "Degradation of Glucagon–Like Peptide–1 by Human Plasma in Vitro Yields and N–Terminally Truncated Peptide That Is a Major Endogenous Metabolite in Vivo", (1995), 80(3): 952–957.

H.A. Smith et al., *Veterinary Pathology* (fourth edition), "Diseases and Disorders of Metabolism: Deficiency Diseases", (1972), p 1018–1020.

G.G. Duncan, *Diseases of Metabolism (Asian edition)*, "Diabetes Mellitus", (1966), p 951–957.

T.J. Kieffer et al., "Degradation of Glucose–Dependent Insulinotropic Polypetide and Truncated Glucagon–Like Peptide 1 In Vitro and In Vivo by DP IV", *Endocrinology*, vol. 136(8), (1995), p 3585–3596.

C.F. Deacon et al., *Diabetes*, "Both Subcutaneously and Intravenously Administered Glucagon–Like Peptide I Are Rapidly Degraded from the $NH_2$–Terminus in Type II Diabetic Patients and in Healthy Subjects", Sep. 1995, 44: 1126–1131.

Pauly et al., *Metabolism*, "Improved Glucose Tolerance in Rats Treated with the Dipeptidyl Peptidase IV (CD26) Inhibitor Ile–Thiazolidide", (1999), 48(3): 385–389.

*Vidal*, (1993), $69^{th}$ Edition, p. 612–613.

*Goodman & Gilman's The Pharmacological Basis of Therapeutics*, Ninth Edition, (1996), p. 1510.

Nathan et al., *Diabetes Care*, "Insulinotropic Action of Glucagonlike Peptide–1–(7–37) in Diabetic and Nondiabetic Subjects", Feb. 1992, 15(2): 270–275.

*Pschyrembel*, Kninisches Wörterbuch 257, Auflage, (1994), 9 pages.

Frohman et al., *Journal of Clin. Invest.*, "Rapid Enzymatic Degradation of Growth Hormone–releasing Hormone by Plasma in Vitro and in Vivo to a Biologically Inactive Product Cleaved at the $NH_2$ Terminus", vol. 78, Oct. 1986, p 906–913.

Snow et al., *Advances In Medicinal Chemistry*, "Boronic Acid Inhibitors of Dipeptidyl Peptidase IV: A New Class of Immunosuppressive Agents", vol. 3, (1995), p 149–177.

Thorens et al., *Diabetes*, "Glucagon–Like Pepetide–I and the Control of Insulin Secretion in the Normal State and in NIDDM", (1993), 42:1219–1225.

Wakselman et al., "Inhibition of HIV–1 infection of CD $26^+$ but not $CD26^-$ cells by a potent cyclopeptidic inhibitor of the DPP IV activity of CD26", Abstract P 44 of the $24^{th}$, *European Peptide Symposium*, (1996).

Ashworth et al., *Bioorg. Med. Chem. Lett.*, "2–Cyanopyrrolidides as Potent, Stable Inhibitors of Dipeptidyl Peptidase IV", (1996), 6(10): 1163–1166.

Endorczi et al., *Acta Physiol. Hung.*, "Dipeptidyl peptidase IV (DP IV) and Superoxide Dismutase Activity in Thymus–Derived Lymphocytes: Effects of Inhibitory Peptides and $Zn^{2+}$ in Vitro", (1990), 75(1):35–44.

Lee, H.S. et al., "Cathepsin B Inhibitor Peptides Derived from β–Casein," *Peptides* 21 (2000) 807–809.

Edwards, J.V. et al., *J. Peptide Res.*, "Synthesis and Activity of $NH_2$ –and COOH–Terminal Elastase Recognition Sequences on Cotton," (1999), 54: 536–543.

Wettstein, J.G. et al. *Pharmacology & Therapeutics*, "Central Nervous System Pharmacology of Neuropeptide Y.", (1995), 65(3): 397–414.

Badia–Elder N.E. et al., *Alcoholism Clinical and Experimental Research*, "Effects of Neuropeptide Y (NPY) on Ethanol Intake and Anxiety in High and Low Alcohol Drinking (HAD1/LAD1) Rats", (2000), 24(5): 82A.

Munglani R. et al., Drugs, *Adis International Ltd*, At, "The Therapeutic Potential of Neuropeptide Y Analgesic, Anxiolytic and Antihypertensive", (1996) 52(3): 371–389.

Wen–Tien Chen et al. "Seprase Complexes in Cellular Invasiveness", *Cancer and Metastatsis Reviews* 22: 259–269, (2003).

Victor A. Gault et al., "Glucose–Dependent Insulinotropic Polypeptide Analogues and Their Therapeutic Potential for the Treatment of Obesity–Diabetes", *Biochemical and Biophysical Research Communications* 308: 207–213, (2003).

Augustyns et al., *Eur. J. Med. Chem.*, "Pyrrolidides: Synthesis and Structure–Activity Relationship as Inhibitors of Dipeptidyl Peptidase IV", (1997), vol. 32, pp. 301–309.

Lader, Malcolm H., MD, "Assessment Methods and the Different Diagnosis of Anxiety", *Journal of Clinical Psychopharmacology*, (1981), vol. 1, No. 6, pp. 342–349.

Winslow, R., "Novartis Drug Alters Picture for Diabetes" *Wall Street Journal*, Wed., Dec. 27, 2000, p. B2.

Ansorge, S., et al., "Membrane–bound peptidases of lymphocytes: Functional implications", *Biomed. Biochim, Acta* 50 (1991) 4–6, pp. 799–807.

Dodge, R.W., et al., "Folding and Unfolding Kinetics of the Proline–to–Alanine Mutants of Bovine Pancreatic Ribonuclease A," *Biochemistry* 1996, 35, pp. 1548–1559.

Demuth, Hans–Ulrich, "Recent Developments in Inhibiting Cysteine and Serine Proteases", *J. Enzyme Inhibition,* 1990, vol. 3, pp. 249–278.

Gomez, S., et al., "Relationship between endo– and exopeptidases in a processing enzyme system: Activation of an endoprotease by the aminopeptidase B–like activity in somatostatin–28 convertase", *Proc. Natl. Acad. Sci. USA,* vol. 85 pp. 5468–5472, Aug. 1988.

Hegen, M., et al., "The T Cell Triggering Molecule Tp103 is Associated with Dipeptidyl Aminopeptidase IV Activity," *The Journal of Immunology,* vol. 144, pp. 2908–2914, No. 8, Apr. 15, 1990.

Ishiura, S., et al., "Identification of a putative amyloid A4–generating enzyme as a prolyl endopeptidase," *Federation of European Biochemical Societies,* vol. 260, No. 1, pp. 131–134, Jan. 1990.

Kräusslich, Hans–Georg, et al., "Viral Proteinases", *Ann. Rev. Biochem.* 1988, 57 pp. 701–754.

Pederson, R.A., et al., "Improved Glucose Tolerance in Zucker Fatty Rats by Oral Administration of the Dipeptidyl Peptidase IV Inhibitor Isoleucine Thiazolidide", *Diabetes,* vol. 47, Aug. 1998 pp. 1253–1258.

Vanhoof, G., et al., "Proline motifs in peptides and their biological processing", The FASEB Journal, vol. 9, Jun. 1995, pp. 736–744.

Walter, R., et al., "Proline Specific Endo– and Exopeptidases", *Molecular & Cellular Biochemistry,* vol. 30, No. 2, Apr. 18, 1980, pp. 111–127.

Kirschke, H. et al., "Proteinases 1: Lysosomal Cysteine Proteinases" *Protein Profile,* vol. 2, Issue 14, 1995, pp. 1583–1634.

Yaron, A., et al., "Proline–Dependent Structural and Biological Properties of Peptides and Proteins" *Critical Reviews in Biochemistry and Molecular Biology,* 28(1), pp. 31–81 (1993).

Vallee et al., "Larval development of Tribolium Confusum in the Presence of Non–Naturally Occurring Amino Acids", Database CAPLUS on STN, Accession No.: 1963:75103, *Annales de l'ACFAS* (1962), 28, p. 26–27 (abstract).

Holst, J. et al., "Inhibition of the Activity of Dipeptidyl–Peptidase IV as a Treatment for Treatment for Type 2 Diabetes", *Diabetes,* 47, 11, Health & Medical Complete pp. 1663–1670, Nov. 1998.

\* cited by examiner

FIG. 1

EFFECTORS OF DIPEPTIDYL PEPTIDASE IV FOR TOPICAL USE

RELATED APPLICATION

This application is a continuation of International Patent Application No. PCT/EP00/08118, filed 20 Aug. 2000, published 1 Mar. 2001 as WO 01/14318, which claims priority to German Patent Application No. DE 199 40 130.6, filed 24 Aug. 1999.

BACKGROUND OF THE INVENTION

1. Field of the Invention

The invention relates to new effectors of dipeptidyl peptidase IV (DP IV) and methods of treatment comprising the topical application thereof. These effectors can be used for targeted influencing of locally limited pathophysiological and physiological processes (inflammation, chemotaxis, autoimmune diseases wound healing), wherein the enzymatic activity and binding activities of dipeptidyl peptidase IV and of enzymes having comparable or identical activity and of proteins having a related primary structure (e.g. FAP, Fibroblast Activation Protein (Levy et al., 1999)) are influenced by means of effectors (substrates, pseudo-substrates, inhibitors, antibodies, binding proteins, binding antagonists, binding agonists, inter alia).

2. Related Art

In addition to proteases involved in non-specific proteolysis, which results, finally, in the breakdown of proteins into amino acids, regulatory proteases are known, which take part in the functionalization (activation, deactivation, modification) of endogenous peptide active substances (Kirschke et al., 1995; Kräusslich and Wimmer, 1987). Especially in the context of immunological research and neuropeptide research, a number of such so-called convertases, signal peptidases or enkephalinases have been discovered (Gomez et al., 1988; Ansorge et al., 1991). Because of the frequency of the presence of the amino acid proline in a multiplicity of peptide hormones and because of the related structural properties of those peptides, a function analogous to the signal peptidases is being discussed for proline-specific peptidases (Yaron and Naider, 1993; Vanhoof et al. 1995). As a result of its particular structure, proline in those peptides determines both the conformation and stability of those peptides, protecting them from breakdown by non-specific proteases (Kessler, 1982). Enzymes that, in contrast, act in highly specific, structure-modifying manner on proline-containing sequences (HIV-protease, cyclophilin, inter alia) are attractive targets for current active substance research. In particular, for the peptidases prolyl endopeptidase (PEP) and dipeptidyl peptidase IV (DP IV), which cleave after the proline, it has been possible to conclude that there probably are connections between modification of the biological activity of natural peptide substrates and selective cleavage thereof by those enzymes. It is accordingly postulated that PEP plays a part in learning and in the memory process and that DP IV is involved in signal transmission during the immune response (Ishiura et al., 1989; Hegen et al., 1990).

DP IV activity and DP IV-analogous activity (for example, the lysosomal DP II has a substrate specificity that is almost identical to DP IV) is to be found in the bloodstream and in almost all organs, where it cleaves dipeptides from the N terminus of biologically active peptides with high specificity when their sequence contains proline or alanine as residues adjacent to the N-terminal amino acid. It is therefore assumed that this enzyme is involved in regulating the biological activity of polypeptides in vivo (Vanhoof et al., 1995).

It has recently been shown that a series of chemokines (RANTES, SDF-1 alpha, MDC, eotaxin, inter alia) are substrates of DP IV and that they are modulated in their function by DP IV (Proost et al., 1998; Proost et al., 1998; Proost et al., 1999; Shioda et al., 1998). As a result of their chemotactic action, chemokines are substantially involved in the regulation of local immunological processes, such as autoimmune processes, inflammation and wound healing (Nelson and Krensky, 1998). In more recent work, we have been able to demonstrate that biologically active peptides having serine or threonine in the $P_1$-position (glucagon, VIP, PACAP) are also substrates of DP IV.

A series of biologically active DP IV-substrates (substance P, somatostatin, VIP, PACAP, inter alia) are involved in the regulation of neuronal, immunological and vasoactive processes in the skin (Scholzen et al., 1998); (Wallengren, 1997). Dipeptidyl peptidase IV accordingly represents an important control centre in regulating the activity of gastrointestinally, immunologically and neurologically active peptides and, consequently, is an interesting therapeutic target (Augustyns et al., 1999). The precise details of the signal cascades have not, however, been clarified fully.

The role of DP IV in the regulation of blood sugar is known in greater detail. As a result of limited proteolysis, the incretins $GIP_{1-4}$ and $GLP-1_{7-37}$ are inactivated. Inhibition of plasma-DP IV activity leads, by way of prolonged activity of the incretins and increased insulin release, to normalization of the blood sugar level (Demuth et al., 1996; Pauly et al., 1996; Pauly et al., 1999).

The role of DP IV in the immune system has not yet been fully clarified. It is an activation marker of T-lymphocytes and a receptor for adenosinedeaminase. The use of DP IV-inhibitors has immunosuppressant effects in cell culture and in vivo (Ansorge et al., 1995; Reinhold et al., 1997; Kubota et al., 1992). Using monoclonal antibodies against CD26, stimulatory effects on intracellular signal cascades ($Ca^{2+}$ influx, kinase activations) have been obtained, in some cases independently of the enzymatic activity of the enzyme (Hegen et al., 1993; Kameoka et al, 1995; Tanaka et al., 1993; Kähne et al., 1995).

Lysyl-prolyl analogues derived from the N-terminal sequence of substance P have shown a wound-healing-promoting effect, which is attributed to the structural similarity to substance P. In contrast, irreversible DP IV-inhibitors used systemically have resulted in inhibition of wound healing (Buntroek et al., 1988; Kohl et al., 1991; Kohl et al., 1989).

In addition to the use of DP IV-inhibitors for the normalization of blood glucose, DP IV-inhibitors have hitherto been used systemically for treating arthritis in an animal model.

In arthritis patients and in animal arthritis models, a reduction in DP IV activity has been observed (Küllertz and Boigk, 1986; Fujita et al., 1992). In particular, as a result of oral or subcutaneous administration of systemically acting DP IV-inhibitors, suppression of alkyldiamine-induced arthritis has been achieved in an animal model (Tanaka et al., 1997; Tanaka et al., 1998).

In relation to other autoimmune diseases as well, an effect has been obtained using DP IV-inhibitors. For example, as a result of DP IV inhibition it has been possible to achieve suppression of the proliferation of myelin basic protein-specific T cell clones (Reinhold et al., 1998).

In the case of various skin diseases (psoriasis, lichen planus) and cancerigenic diseases of the skin, it has been possible to demonstrate increased DP IV activity in keratinocytes and fibroblasts (Novelli et al., 1996; Raynaud et al., 1992).

Fibroblast activation protein, which is closely related to DP IV, having approximately 50% sequence homology with respect to DP IV, and which is probably the same as the seprase described by Piñieiro-Sanchez et al., 1997, is also expressed to an increased extent by inactivated fibroblasts of epithelial carcinomas and healing wounds (Niedermeyer et al., 1998).

Because of the wide distribution of the protein in the body and the wide variety of mechanisms involving DP IV, DP IV activities and DP IV-related proteins, systemic therapy (enteral or parenteral administration) with DP IV-inhibitors can result in a series of undesirable side-effects. For example, parenteral or enteral administration of DP IV-inhibitors will intervene in a regulating or deregulating manner in glucose metabolism.

It has now been possible to show that side chain-modified substrates of the enzyme dipeptidyl peptidase IV can be recognized by the enzyme and cleaved in the same way as unmodified substrates (Demuth, H.-U., Heins, J., 1995).

For example, it has been possible to show that phosphorylated dipeptide-(B)-p-nitroanilides (KASPARI, A, et al., 1996) are substrates of DP IV. DP IV-inhibitors such as, for example, Glu(Gly)-Thia or Lys(Z-NO$_2$)-Thia (Reinhold, D., et al., 1998) are transported completely.

BRIEF SUMMARY OF THE INVENTION

The problem to be solved consisted in preparing compounds that can be used for targeted influencing of locally limited pathophysiological and physiological processes. The problem of the invention especially consists in obtaining locally limited inhibition of DP IV or DP IV-analogous activity for the purpose of targeted intervention in the regulation of the activity of locally active peptide hormones.

The problem is solved according to the invention by providing compounds of the general formula:

Wherein
A is an amino acid having at least one functional group in the side chain,
B is a chemical compound covalently bound to at least one functional group of the side chain of A, chosen from the group consisting of:
  oligopeptides having a chain length of up to 20 amino acids, excluding homopolymers of glycine consisting of up to 6 glycine monomers, and
  polyethylene glycols having molar masses of up to 20,000 g/mol, and
C is a thiazolidine, pyrrolidine, cyanopyrrolidine, hydroxyproline, dehydroproline or piperidine group amide-bonded to A.

In accordance with the invention, at least one pharmaceutical composition is especially provided which comprises at least one compound of the general formula:

wherein
A is an amino acid, preferably an α-amino acid, especially a natural α-amino acid having at least one functional group in the side chain, preferably threonine, tyrosine, serine, arginine, lysine, aspartic acid, glutamic acid or cysteine,
B is a chemical compound covalently bound to at least one functional group in the side chain of A, namely oligopeptides having a chain length of up to 20 amino acids, polyethylene glycols having molar masses of up to 20 000 g/tool, optionally substituted organic amines, amides, alcohols, acids or aromatic compounds having from 8 to 50 C atoms,
C is a thiazolidine, pyrrolidine, cyanopyrrolidine, hydroxyproline, dehydroproline or piperidine group amide-bonded to A, and
at least one customary adjuvant appropriate for the site of action.

Furthermore, such compounds or pharmaceutical compositions are used for influencing topically especially reducing the activity of dipeptidyl peptidase IV or analogous enzymes. Such compounds or pharmaceutical compositions may be used in the form of an ointment, cream, cosmetic, patch, dressing, drops, spray, inhalation, implant or injection solution.

BRIEF DESCRIPTION OF THE DRAWING

The course, over time, of the percentage inhibition of plasma-DP IV activity following oral administration of 5 μmol of inhibitor per 300 g of rat (n=2) is shown.

DETAILED DESCRIPTION OF THE INVENTION

Throughout the description and the claims, the expression "alkyl" can denote a $C_{1-50}$alkyl group, preferably a $C_{1-30}$alkyl group, especially a $C_{8-12}$alkyl group; for example, an alkyl group may be a methyl, ethyl, propyl, isopropyl or butyl group. The expression "alk", for example in the expression "alkoxy", and the expression "alkan", for example in the expression "alkanoyl", are defined as for "alkyl".

Aromatic compounds are preferably substituted or optionally unsubstituted phenyl, benzyl, naphthyl, biphenyl or anthracene groups, which preferably have at least 8 C atoms.

The expression "alkenyl" can denote a $C_{2-10}$alkenyl group, preferably a $C_{2-6}$alkenyl group, which has the double bond(s) at any desired location and may be substituted or unsubstituted.

The expression "alkynyl" can denote a $C_{2-10}$alkynyl group, preferably a $C_{2-6}$alkynyl group, which has the triple bond(s) at any desired location and may be substituted or unsubstituted.

The expression "substituted" or substituent can denote any desired substitution by one or more, preferably one or two, alkyl, alkenyl, alkynyl, mono- or multi-valent acyl, alkanoyl, alkoxyalkanoyl or alkoxyalkyl groups; the aforementioned substituents may in turn have one or more (but preferably zero) alkyl, alkenyl, alkynyl, mono- or multi-valent acyl, alkanoyl, alkoxyalkanoyl or alkoxyalkyl groups as side groups.

Organic amines, amides, alcohols or acids, each having from 8 to 50 C atoms, preferably from 10 to 20 C atoms, can have the formulae (alkyl)$_2$N—  or alkyl-NH—, —CO—N(alkyl)$_2$ or —CO—NH(alkyl), -alkyl-OH or -alkyl-COOH.

Despite an extended side chain function, the compounds according to the invention can still bind to the active centre of the enzyme dipeptidyl peptidase IV and analogous enzymes but are no longer actively transported by the peptide transporter PepT1. The resulting reduced or greatly restricted transportability of the compounds according to the invention leads, in ideal manner, to local, topical inhibition of DP IV and of analogous enzymes.

The compounds according to the invention or compounds used in accordance with the invention can be present or used, respectively, in the form of racemates or in the form of enantiomerically pure compounds, preferably in the L-threo or L-allo form with respect to A.

Local intervention in the regulation of peptide hormones by means of topical administration of specific DP IV-inhibitors accordingly makes it possible to avoid systemic side-effects caused by enteral or parenteral administration of DP IV-inhibitors, because only locally limited inhibition of DP IV activity takes place. Systemic regulation processes or regulation processes in other tissues remain unaffected to a very considerable extent because rapid systemic distribution of the compounds is avoided.

By extending/expanding the side chain modifications, for example beyond a number of seven carbon atoms, it is accordingly possible in accordance with the invention to obtain a dramatic reduction in transportability (Table 1). The Examples in Table 1 clearly show that, with increasing spatial size of the side chains, there is a reduction in the transportability of the substances. By spatially and sterically expanding the side chains, for example beyond the atom group size of a monosubstituted phenyl radical, hydroxylamine radical or amino acid residue, it is possible according to the invention to modify or suppress the transportability of the target substances.

It is accordingly possible to influence DP IV activity in the living body in discriminating manner.

By means of the invention, it is accordingly possible, on the one hand, to achieve effective action of the inhibitors in the tissue to be treated and, on the other hand, by virtue of locally limited, that is to say topical, administration of DP IV-inhibitors it is possible to avoid systemic actions of the inhibitors to a very considerable extent. It is accordingly possible to influence local physiological and pathophysiological processes (inflammation, psoriasis, arthritis, autoimmune diseases, allergies) effectively and with few side-effects.

The invention is supported by the following facts:

DP IV-inhibitors administered enterally and parenterally, that is to say orally and intravenously or subcutaneously, are distributed systemically and inhibit DP IV and analogous activities throughout the body.

A series of bioactive peptide substrates of DP IV are, however, involved in the regulation of local signal cascades (chemotaxis, inflammation, neurotransmission).

The side chain-modified DP IV-inhibitors according to the invention exhibit, surprisingly, high inhibitory potency, but are absorbed and transported hardly at all or not at all and consequently do not result in demonstrable systemic effects.

The invention therefore makes available new DP IV-inhibitors and a novel approach for the use of DP IV-inhibitors in vivo. Such inhibitors can be matched to the type of use by means of chemical modifications and/or formulations. For example, systemic distribution is made difficult or prevented by means of voluminous hydrophilic substitutions on the side chain.

The inhibitors can be administered in pharmaceutical and cosmetic preparations. Topical use encompasses local use of the inhibitors by direct application to the tissue to be treated (e.g. skin, wounds, tumours) by means of ointments, creams or cosmetics, and indirect application by means of effector-containing patches, dressings or the like, by application in parts of the body (mouth, nose, ears, eyes, lungs) in the form of drops, sprays, inhalations or the like, by direct injection into or around the tissue to be treated and by implantation of effector-containing materials. Topical use further encompasses oral or anal administration of non-absorbable or not readily absorbable effectors of dipeptidyl peptidase IV or of DP IV-analogous sequences for the purpose of selectively influencing gastrointestinal DP IV.

In accordance with the invention, there are especially used compounds wherein the oligopeptides have chain lengths of from 3 to 15, especially from 4 to 10, amino acids, and/or the polyethylene glycols have molar masses of at least 250 g/mol, preferably of at least 1500 g/mol and up to 15,000 g/mol, and/or the optionally substituted organic amines, amides, alcohols, acids or aromatic compounds have at least 12 C atoms and preferably up to 30 C atoms. Furthermore, there are disclosed pharmaceutical and cosmetic compositions that comprise at least one compound according to the invention, optionally in combination with carriers or adjuvants customary per se.

The compounds or pharmaceutical or cosmetic compositions according to the invention can be used for topically influencing the activity of dipeptidyl peptidase IV or of analogous enzymes, especially for the prophylaxis or therapy of diseases of the skin or mucosa, autoimmune diseases and inflammation such as, for example, psoriasis, allergies, arthritis, tumours or autoimmune diseases.

The compounds and pharmaceutical or cosmetic compositions can be formulated and used in the form of an ointment, cream, cosmetic, patch, dressing, drops, spray, inhalation, implant or injection solution.

The adjuvants used in accordance with the invention are known per se. The invention accordingly relates to the topical use of effectors of dipeptidyl peptidase IV and of DP IV-analogous enzyme activities and of DP IV-like proteins. Topical use allows local modification of the activities of the afore-mentioned highly specific enzymes which are crucially involved in inactivation and activation of biologically active peptides (chemokines, substance P, VIP, PHM, PACAP, growth factors, inter alia).

Targeted intervention in local immunological processes (chemotaxis, inflammatory processes, autoimmune diseases) is accordingly possible, as well as effective and targeted treatment of pathophysiological and physiological processes related thereto (psoriasis, periodontitis, arthritis, allergies, inflammation). The invention makes it possible for the inhibitors to be used simply and in high local concentrations. As a result of low systemic loading with the corresponding effectors, an influence on the incretin system or systemic immune response is avoided.

EXAMPLES

Example 1

Action of Side Chain-Modified Glutamylthiazolidines as Non-Readily-Transportable DP IV-Inhibitors

Side chain-modified glutamylthiazolidines having a structure H-Glu(X)-Thia were synthesized, with polyethylene glycol or glycine oligomers of various chain lengths being used as X (see Method A for description of synthesis). The binding characteristics of those derivatives and their transportability by the peptide transporter PepT1 were investigated and the $K_i$ values with respect to DP IV were determined (Table 1).

It was found, surprisingly, that the side chain modifications modify the binding characteristics to the compound only to a slight extent. In contrast, the ability of the inhibitors to be tranported by the peptide transporter is dramatically diminished by the side chain modification.

The said DP IV-inhibitors are therefore excellently suited to achieving locally limited (topical) inhibition of DP IV in the body.

TABLE 1

Transportability and inhibitor constants of selected DP IV-inhibitors.

| Compound | $EC_{50}$ (mM)[1] | $I_{max}$ (HA)[2] | $K_i$ (mol/l)[3] |
|---|---|---|---|
| amino acid thiazolidides | | | |
| H-Ile-Thia | 0.98 | 25 ± 8 | 1.3e-7 ± 11.1% |
| H-Glu-Thia | 1.1 | 35 ± 13 | 6.1e-7 ± 11.4% |
| side chain-modified glutamylthiazolidines | | | |
| H-Gly(NHOH)-Thia | 3.18 | 42 ± 11 | 1.7e-6 ± 8.6% |
| H-Glu(Gly$_3$)-Thia | 8.54 | n.d.[4] | 1.92e-7 ± 8.4% |
| H-Glu(Gly$_5$)-Thia | >10 | n.d.[4] | 9.93e-8 ± 11.4% |
| H-Glu(PEG)-Thia | >10 | n.d.[4] | 3.11e-6 ± 9.8% |

[1]Effective concentrations of the compounds inhibiting the binding of
[3]H-D-Phe-Ala (80 mM) to PepT1-expressing *P. pastoris* cells by 50% ($EC_{50}$ values).
[2]Transport characteristics at PepT1-expressing oocytes of *X. leavis* - by means of two-electrode voltage clamp method, I = inward currents generated by the transport.
[3]Inhibitor constants for competitive inhibition of purified kidney-DP IV by the compounds of the examples.
[4]Not detectable.

Example 2

Effect of Orally Administered DP IV-Inhibitors on Activity of Serum-DP IV

Figure 1:
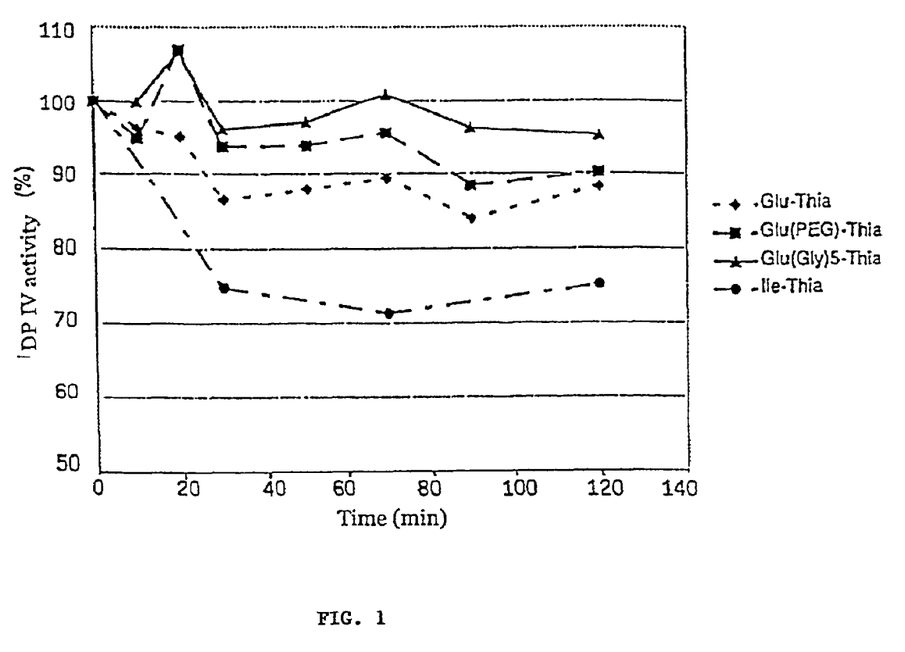
FIG. 1: Systemic action of orally administered DP IV-inhibitors in healthy Wistar rats.

The inhibition of plasma-DP IV (systemic action) was investigated following oral administration of side chain-modified DP IV-inhibitors (5 µM/300 mg rat) compared with unmodified inhibitors in healthy Wistar rats.

Although the inhibitors have approximately equal $K_i$ values to DP IV (Table 1), plasma-DP IV is inhibited by the novel side chain-modified inhibitors much more slowly and to a much lesser extent overall. This means that the inhibitors are absorbed from the intestine much less readily or not at all. In the case of Glu(Gly)$_5$-Thia, especially, no systemic action of the orally administered active ingredient is detectable.

Those inhibitors may consequently act as basic structures for the synthesis of novel topically administrable DP IV-inhibitors without systemic action.

Example 3

Synthesis of Side Chain-Modified Inhibitors of DP IV

3.1 Synthesis of Boc-Glu-Thia.

Reaction of Boc-Glu(OMe)-OH with Thia*HCl according to Method B (see section 3.4 for methods), hydrolysis of Boc-Glu(OMc)-Thia according to Method G.

TABLE 2

Analytical data for Boc-Glu-Thia.

| Compound | Empirical formula $M_r$ Synthesis method Yield | MS [M + H]+ TLC: $R_f$/system m.p. | $[\alpha]^{20}$D Concentration Solvent | Elemental analysis (calc./ found) % | HPLC $R_t$ [min]/ system |
|---|---|---|---|---|---|
| Boc-Glu-Thia | $C_{13}H_{22}N_2O_5S$ 318.38 B + G 62% | 319.5 0.52/A[1] 0.42/B[1] 115–118° C. | -3.1 C = 1 methanol | C: 49.04/ 48.89 H: 6.96/ 6.82 N: 8.80/ 8.59 | 13.93/ A[2] |

[1]Thin-layer chromatography
System A: chloroform/methanol 90:10
System B: benzene/acetone/acetic acid 25:10:0.5
System C: n-butanol/EA/acetic acid/$H_2O$ 1:1:1:1
[2]HPLC separation conditions:
Column: Nucleosil C-18, 7µ, 250 mm × 21 mm; eluant: isocratic, 40% ACN/water/0.1% TFA; flow rate: 6 ml/min; λ. = 220 nm.

3.2 Side Chain-Modified Boc-glutamylthiazolidines.

Boc-Glu-Thia was modified at the γ-carboxylic acid function by introducing radicals of varying size. The radicals were coupled by way of their amino group by forming an amide bond to the γ-carboxylic acid function, with a variety of coupling methods being used depending on the radical.

The following amino components were attached to Boc-Glu-Thia using the method stated:

| Amino component | Coupling methods (see §3.4) | Yields |
|---|---|---|
| Polyethylene glycol amine ($M_r \approx$ 8000) | C | 93% |
| H-Gly-Gly-Gly-OH | D + E | 49% |
| H-Gly-Gly-Gly-Gly-Gly-OH | D + E | 86% |

In 2 cases, purification of the reaction products differs from the general description of synthesis:

1. Boc-Glu(Gly$_5$)-Thia: The product already precipitates out from the mixture on stirring overnight; it is subsequently filtered off and washed with 0.1N HCl and copious amounts of water. It is then dried over $P_4O_{10}$ in vacuo.
2. Boc-Glu(PEG)-Thia: In contrast to the general procedure, the starting materials for the synthesis are dissolved in a 500-fold excess of DMF. After the reaction is complete, the DMF is completely removed in vacuo and the residue is dissolved in a large amount of methanol. After ether is poured on, to form an upper layer, the product precipitates out together with the unreacted PEG. Fine purification was carried out by preparative HPLC separation on a gel filtration column (Pharmacia, Sephadex G-25, 90 µm, 260 mm–100 mm; Separating conditions: eluant: water; flow rate: 5 ml/min; λ=220 nm.)

TABLE 3

Synthesis data for side chain-modified Boc-glutamylthiazolidines.

| Compound | Empirical Formula $M_r$ Yield | MS[M + H]+ TLC/$R_f$/ System m.p. | $[\alpha]^{20}D$ Concentration Solvent | Elemental analysis calc./ found) % | HPLC $R_t$ [min]/system |
|---|---|---|---|---|---|
| Boc-Glu(Gly$_3$)-Thia | $C_{19}H_{31}N_5O_8S$ 489.54 49% | 490.5 | | C: 46.62 H: 6.38 N: 14.31 | |
| Boc-Glu(Gly$_5$)-Thia | $C_{23}H_{37}N_7O_{10}S$ 603.64 86% | 604.5 0.09/C decomp. from 202° C. | n.d.[1] | C: 45.76/45.60 H: 6.18/6.11 N: 16.24/16.56 | 11.93/A[2] |
| Boc-Glu(PEG)-Thia | 93% | ≈8000 mass emphasis) 52–53° C. | n.d.[1] | n.d.[1] | n.d.[1] |

[1]Not determined, or not determinable.
[2]HPLC separation conditions
Column: Nucleosil C-18, 7µ, 250 mm × 21 mm
Eluant: isocratic, 40% ACN/water/0.1% TFA; Flow rate: 6 ml/min; λ = 220 nm.

3.3 Side Chain-Modified Glutamylthiazolidines.

The N-terminal Boc protecting groups were cleaved off the compounds described in Table 3 using method F. The substances modified with Gly derivatives were purified by preparative HPLC separation and are present as trifluoroacetates. The H-Glu(PEG)-Thia was purified on a gel filtration column in the same manner as the Boc-protected precursor.

TABLE 4

Synthesis data for side chain-modified glutamylthiazolidines.

| Compound | Empirical Formula $M_r$ Yield | MS [M + H]+ TLC/$R_f$/ System m.p. | $[\alpha]^{20}D$ Concentration Solvent | Elemental analysis (calc./ found) % | HPLC $R_t$ [min]/ system |
|---|---|---|---|---|---|
| H-Glu(Gly$_3$) Thia *TFA | $C_{16}H_{24}N_5O_8SF_3$ 503.45 94% | 503.45 0.32/C 91–94° C. | =4.1 c = 1 methanol | C: 38.17/37.56 H: 4.80/4.78 N: 13.91/13.43 | 7.84/C[2] |
| H-Glu(Gly$_5$) Thia *TFA | $C_{20}H_{30}N_7O_{10}SF_3$ 617.55 98% | 617.55 0.25/C 105–107° C. | n.d.[1] | C: 38.90/38.82 H: 4.90/4.79 N: 15.88/15.39 | 8.22/C[2] |
| H-Glu(PEG) Thia *HCl | 92% | ≈8000 (mass emphasis) | n.d.[1] | n.d.[1] | n.d.[1] |

[1]Not determined or not determinable.
[2]HPLC separation conditions
Column: Nucleosil C-18, 7µ, 250 mm × 21 mm
Eluant: ACN/water/0.1% TFA
Gradient: 20% ACN → 90% ACN over 30 min; Flow rate: 6 ml/min; λ = 220 nm.

3.4 General Synthesis Procedures.

Method A: Peptide Bond Attachment by the Mixed Anhydride Method Using CFIBE as Activation Reagent.

10 mmol of N-terminally protected amino acid or peptide are dissolved in 20 ml of absolute THF. The solution is cooled to −15° C. ±2° C. With stirring in each case, 10 mmol of N-MM and 10 mmol of chloroformic acid isobutyl ester are added in succession, the stated temperature range being strictly adhered to. After approximately 6 min, 10 mmol of the amino component are added. When the amino component is a salt, a further 10 mmol of N-MM are then added to the reaction mixture. The reaction mixture is then stirred for 2 h in the cold state and overnight at room temperature.

The reaction mixture is concentrated using a rotary evaporator, taken up in EA, washed with 5% KH$_2$SO$_4$ solution, saturated NaHCO$_3$ solution and saturated NaCl solution and dried over NaSO$_4$. After removal of the solvent in vacuo, the compound is recrystallised from EA/pentane.

Method B: Peptide Bond Attachment by the Mixed Anhydride Method Using Pivalic Acid Chloride as Activation Reagent.

10 mmol of N-terminally protected amino acid or peptide are dissolved in 20 ml of absolute THF. The solution is cooled to 0° C. With stirring in each case, 10 mmol of N-MM and 10 mmol of pivalic acid chloride are added in succession, the stated temperature range being strictly adhered to. After approximately 6 min, the mixture is cooled to −15° C. and, once the lower temperature has been reached, 10 mmol of the amino component are added. When the amino component is a salt, a further 10 mmol of N-MM are then added to the reaction mixture. The reaction mixture is then stirred for 2 h in the cold state and overnight at room temperature. Further working up is carried out as in Method A.

Method C: Peptide Bond Attachment Using TBTU as Activation Reagent.

10 mmol of the N-terminally protected amino acid or peptide and 10 mmol of the C-terminally protected amino component are dissolved in 20 ml of absolute DMF. The solution is cooled to 0° C. With stirring in each case, 10 mmol of DIPEA and 10 mmol of TBTU are added in succession. The reaction mixture is stirred for one hour at 0° C. and then overnight at room temperature. The DMF is completely removed in vacuo and the product is worked up as described in Method A.

Method D: Synthesis of an Active Ester (N-hydroxysuccinimide Ester).

10 mmol of N-terminally protected amino acid or peptide and 10 mmol of N-hydroxy-succinimide are dissolved in 20 ml of absolute THF. The solution is cooled to 0° C. and 10 mmol of dicyclohexylcarbodiimide are added, with stirring. The reaction mixture is stirred for a further 2 h at 0° C. and then overnight at room temperature. The resulting N,N'-dicyclohexylurea is filtered off, the solvent is removed in vacua and the remaining product is recrystallised from EA/pentane.

Method E: Amide Bond Attachment Using N-hydroxysuccinimide Esters.

10 mmol of the C-terminally unprotected amino component are introduced into an $NaHCO_3$ solution (20 mmol in 20 ml of water). At room temperature and with stirring, 10 mmol of the N-terminally protected N-hydroxysuccinimide ester dissolved in 10 ml of dioxane are slowly added dropwise. Stirring of the reaction mixture is continued overnight and the solvent is then removed in vacuo. Further working up is carried out as in Method A.

Method F: Cleavage of the Boc Protecting Group.

3 ml of 1.1N HCl/glacial acetic acid (Method F1) or 3 ml of 1.1N HCl/dioxane (Method F2) or 3 ml of 50% TFA in DCM (Method F3) are added to 1 mmol of Boc-protected amino acid pyrrolidide, thiazolidide or peptide. The cleavage at RT is monitored by means of TLC. After the reaction is complete (approximately 2 h), the compound is precipitated out in the form of the hydrochloride using absolute diethyl ether, is isolated with suction and dried over $P_4O_{10}$ in vacuo. Using methanol/ether, the product is recrystallized or reprecipitated.

Method G: Hydrolysis.

1 mmol of peptide methyl ester is dissolved in 10 ml of acetone and 11 ml of 0.1M NaOH solution and stirred at RT. The course of the hydrolysis is monitored by means of TLC. After the reaction is complete, the acetone is removed in vacuo. The remaining aqueous solution is acidified, using concentrated KH2SO4 solution, until a pH of 2–3 is reached. The product is then extracted several times using EA; the combined ethyl acetate fractions are washed with saturated NaCl solution and dried over $NaSO_4$, and the solvent is removed in vacuo. Crystallization from EA/pentane is carried out.

BIBLIOGRAPHY

Ansorge, S., Schön, E., and Kunz, D. (1991). Membrane-bound peptidases of lymphocytes: functional implications. Biomed. Biochim. Acta 50, 799–807.

Ansorge, S., Bühling, F., Hoffmann, T., Kähne, T., Neubert, K., and Reinhold, D. (1995). Di-peptidylpeptidase IV (CD26) in metabolism and the immune response (Fleischer, B., Ed) Springer-Verlag, Heidelberg. 163–184.

Augustyns, K., Bal, G., Thonus, G., Belyaev, A., Zhang, X. M., Bollaert, W., Lambeir, A. M., Durinx, C., Goossens, F., and Haemers, A. (1999). The unique properties of dipeptidyl-peptidase IV (DPP IV/CD26) and the therapeutic potential of DPP IV inhibitors. Curr Medicinal Chem 6, 311–327.

Buntrock, P., Neubert, K., Kohl, A., Moch, C., Born, I., Demuth, H.-U., and Barth, A. (1988). Stimulation and inhibition of wound healing process using short-chain peptides. Biol. Zent. bl 107, 87–92.

Demuth, H.-U., Heins, J., On the catalytic Mechanism of Dipeptidyl Peptidase IV. in Dipeptidyl Peptidase IV, Fleischer, Ed., R. G.Landes, Biomedical Publishers, Georgetown, 1, 1995.

Demuth, H.-U., McIntosh, C. H. S., Rosche, F., Pauly, R. P., Pederson, R. A., and Schmidt, J. Verfahren zur Senkung des Blutglukosespiegels in Säugern. DE 196 16 486.9

Fujita, K., Hagihara, M., Nagatsu, T., Iwata, H., and Miura, T. (1992). The activity of dipeptidyl peptidase II and dipeptidyl peptidase IV in mice immunized with type II collagen. Bio-chem. Med. Metab. Biol. 48, 227–234.

Gomez, S., Gluschankof, P., Lepage, A., and Cohen, P. (1988). Relationship between endo- and exopeptidases in a processing enzyme system: activation of an endoprotease by the ami-nopeptidase B-like activity in somatostatin-28 convertase. Proc Natl Acad Sci USA 85, 5468–5472.

Hegen, M., Niedobitek, G., Klein, C. E., Stein, H., and Fleischer, B. (1990). The T cell triggering molecule Tp103 is associated with dipeptidyl aminopeptidase IV activity. J. Immunol. 144, 2908–2914.

Hegen, M., Mittrucker, H.-W., Hug, R, Demuth, H. U., Neubert, K., Barth, A., and Fleischer, B. (1993). Enzymatic activity of CD26 (dipeptidylpeptidase IV) is not required for its signalling function in T cells. Immunobiol. 189, 483–493.

Ishiura, S., Tsukahara, T., Tabira, T., and Sugita, H. (1989). Putative N-terminal splitting enzyme of amyloid A4 peptides is the multicatalytic proteinase, ingensin, which is widely distributed in mammalian cells. FEBS Lett 257, 388–392.

Kameoka, J., Sato, T., Torimoto, Y., Sugita, K., Soiffer, R. J., Schlossman, S. F., Ritz, J., and Morimoto, C. (1995). Differential CD26-mediated activation of the CD3 and CD2 pathways after CD6-depleted allogeneic bone marrow transplantation. Blood 85, 1132–1137.

Kähne, T., Neubert, K., and Ansorge, S. (1995). Enzymatic activity of DPIV/CD26 is involved in PMA-induced hyperphosphorylation of $p56^{lck}$ Immunol. Lett. 46, 189–193.

Kaspari, A., Diefenthal, T., Grosche, G., Schierhorn, A., Demuth, H.-U., Substrates containing phosphorylated residues adjacent to proline decrease cleavage by proline-specific pepti-dases, Protein Struct Mol Enzym, 147, 1996

Kessler, H. (1982). Konformation und biologische Wirkung von zyklischen Peptiden. Angew. Chem. 94, 509

Kirschke, H., Barrett, A. J., and Rawlings, N. D. (1995). Proteinases 1: lysosomal cysteine pro-teinases. Protein Profile 2, 1581–1643.

Kohl, A., Volk, H. D., Diezel, W., Buntrock, P., and Diamantstein, T. (1989). The dipeptide Lys-Pro restores the diminished wound healing following treatment with anti-T-helper cell monoclonal antibody. Int. J. Immunopharmacol. 11, 237–240.

Kohl, A., Volk, H. D., Buntrock, P., Kohl, G., Diamantstein, T., and von Baehr, R. (1991). The role of dipeptidylpep-tidase IV positive T cells in wound healing and angiogenesis. Agents Actions 32, 125–127.

Kräusslich, H.-G. and Wimmer, E. (1987). Viral Proteinases. Ann. Rev. Biochem. 57, 701

Kubota, T., Flentke, G. R., Bachovchin, W. W., and Stollar, B. D. (1992). Involvement of dipep-tidyl peptidase IV in an in vivo immune response. Clin. Exp. Immunol. 89, 192–197.

Küllertz, G. and Boigk, J. (1986). Dipeptidyl peptidase IV activity in the serum and synovia of patients with rheumatoid arthritis. Z Rheumatol 45, 52–56.

Levy, M. T., McCaughan, G. W., Abbott, C. A., Park, J. E., Cunningham, A. M., Müller, E., Rettig, W. J., Gorell, M. D., Fibroblast Activation Protein: A Cell Surface Dipeptidyl Peptidase and Gelatinase Expressed by Stellate Cells at the Tissue Remodelling Interface in Human Cirrhosis *Hepatology,* 29, 1999, 1768–1778.

Nelson, P. J. and Krensky, A. M. (1998). Chemokines, lymphocytes and viruses: what goes around, comes around. *Curr Opin Immunol* 10, 265–270.

Niedermeyer, J., Enenkel, B., Park, J. E., Lenter, M., Rettig, W. J., Damm, K., and Schnapp, A. (1998). Mouse fibroblast-activation protein—Conserved Fap gene organization and bio-chemical function as a serine protease. *Eur J Biochem* 254, 650–654.

Novelli, M., Savoia, P., Fierro, M. T., Verrone, A., Quaglino, P., and Bemengo, M. G. (1996). Keratinocytes express dipeptidyl-peptidase IV (CD26) in benign and malignant skin diseases. *Br J Dermatol* 134, 1052–1056.

Pauly, R. P., Demuth, H. U., Rosche, F., Schmidt, J., White, H. A., Lynn, F., McIntosh, C. H. S., and Pederson, R. A. (1999). Improved glucose tolerance in rats treated with the dipepti-dyl peptidase IV (CD26) inhibitor ile-thiazolidide. *Metabolism* 48, 385–389.

Pauly, R. P., Rosche, F., Wermann, M., McIntosh, C. H. S., Pederson, R. A., and Demuth, H. U. (1996). Investigation of glucose-dependent insulinotropic polypeptide-(1-42) and gluca-gon-like peptide-1-(7-36) degradation in vitro by dipeptidyl peptidase IV using matrix-assisted laser desorption/ionization time of flight mass spectrometry—A novel kinetic approach. *J Biol Chem* 271, 23222–23229.

Proost P., De Meester, I., Schols, D., Struyf, S., Lambeir, A. M., Wuyts, A., Opdenakker, G., De Clercq, E., Scharpe, S., and Van Damme, J. (1998a). Amino-terminal truncation of che-mokines by CD26/dipeptidyl-peptidase IV. Conversion of RANTES into a potent inhibitor of monocyte chemotaxis and HIV-1-infection. *J Biol Chem* 273, 7222–7227.

Proost, P., Struyf, S., Schols, D., Durinx, C., Wuyts, A., Lenaerts, J. P., De Clercq, E., De Mee-ster, I., and Van Damme, J. (1998b). Processing by CD26-dipeptidyl-peptidase IV redu-ces the chemotactic and anti-HIV-1 activity of stromal-cell-derived factor-1alpha. *FEBS Lett* 432, 73–76.

Proost, P., Struyf, S., Schols, D., Opdenakker, G., Sozzani, S., Allavena, P., Mantovani, A., Au-gustyns, K., Bal, G., Haemers, A., Lambeir, A. M., Scharpe, S., Van Damme, J., and De Meester, I. (1999). Truncation of macrophage-derived chemokine by CD26-dipeptidyl-peptidase IV beyond its predicted cleavage site affects chemotactic activity and CC che-mokine receptor 4 interaction. *J Biol Chem* 274, 3988–3993.

Raynaud, F., Bauvois, B., Gerbaud, P., and Evain Brion, D. (1992). Characterization of specific proteases associated with the surface of human skin fibroblasts, and their modulation in pathology. *J. Cell. Physiol.* 151, 378–385.

Reinhold, D., Bank, U., Buhling, F., Tager, M., Born, I., Faust, J., Neubert, K., and Ansorge, S. (1997). Inhibitors of dipeptidyl peptidase IV (DP IV, CD26) induces secretion of trans-forming growth factor-beta 1 (TGF-beta 1) in stimulated mouse splenocytes and thy-mocytes. *Immunol Lett* 58, 29–35.

Reinhold, D., Hemmer, B., Gran, B., Born, I., Faust, J., Neubert, K., McFarland, H. F., Martin, R., and Ansorge, S. (1998). Inhibitors of dipeptidyl peptidase IV/CD26 suppress activa-tion of human MBP-specific CD4+T cell clones. *J Neuroimmunol* 87, 203–209.

Reinhold D., Hemmer, B., Steinbrecher, A., Born, I., Faust, J., Neubert, K., Brocke, S., Martin, R., Ansorge, S., Dipeptidyl Peptidase IV (CD 26): Role in T cell activation and autoim-mune disease. Biol. Chem 379, S 69, 1998.

Scholzen, T., Armstrong, C. A., Bunnett, N. W., Luger, T. A., Olerud, J. E., and Ansel, J. C. (1998). Neuropeptides in the skin: interactions between the neuroendocrine and the skin immune systems. *Exp Dermatol* 7, 81–96.

Shioda, T., Kato, H., Ohnishi, Y., Tashiro, K., Ikegawa, M., Nakayama, E. E., Hu, H., Kato, A., Sakai, Y., Liu, H., Honjo, T., Nomoto, A., Iwamoto, A., Morimoto, C., and Nagai, Y. (1998). Anti-HIV-1 and chemotactic activities of human stromal cell-derived factor 1alpha (SDF-1alpha) and SDF-1beta are abolished by CD26-dipeptidyl peptidase IV-me-diated cleavage. *Proc Natl Acad Sci USA* 95, 6331–6336.

Tanaka, T., Kameoka, J., Yaron, A, Schlossman, S. F., and Morimoto, C. (1993). The costimu-latory activity of the CD26 antigen requires dipeptidyl peptidase IV enzymatic activity. *Proc. Natl. Acad. Sci. U.S.A.* 90, 4586–4590.

Tanaka, S., Murakami, T., Horikawa, H., Sugiura, M., Kawashima, K., and Sugita, T. (1997). Suppression of arthritis by the inhibitors of dipeptidyl peptidase IV. *Int J Immunophar-macol* 19, 15–24.

Tanaka, S., Murakami, T., Nonaka, N., Ohnuki, T., Yamada, M., and Sugita, T. (1998). Anti-arthritic effects of the novel dipeptidyl peptidase IV inhibitors TMC-2A and TSL-225. *Immunophannacology* 40, 21–26.

Vanhoof, G., Goossens, F., De Meester I, Hendriks, D., and Scharpe, S. (1995). Proline motifs in peptides and their biological processing. *FASEB J.* 9, 736–744.

Wallengren, J. (1997). Vasoactive peptides in the skin. *J Investig Dermatol Symp Proc* 2, 49–55.

Yaron, A. and Naider, F. (1993). Proline-dependent structural and biological properties of peptides and proteins. *Crit. Rev. Biochem. Mol. Biol.* 28(1), 31–38.

What is claimed is:

1. A dipeptidyl peptidase IV (DP-IV) inhibitor compound of the general formula wherein A is an amino acid having at least one functional group in the side chain, B is a chemical compound covalently bound to at least one functional group of the side chain of A, chosen from the group consisting of:
  (a) oligopeptides having a chain length of up to 20 amino acids, except for homopolymers of glycine consisting of up to 6 glycine monomers, and
  (b) polyethylene glycols having molar masses of up to 20 000 g/mol; and C is a group amide-bonded to A, chosen from the group consisting of thiazolidine, pyrrolidine, cyanopyrrolidine, hydroxyproline, dehydroproline and piperidine.

2. The compound according to claim 1, wherein A is an α-amino acid.

3. The compound according to claim 2, wherein A is a natural α-amino acid.

4. The compound according to claim 1, wherein the amino acid of A is chosen from the group consisting of threonine, tyrosine, serine, arginine, lysine, aspartic acid, glutamic acid and cysteine.

5. The compound according to claim 1, wherein the oligopeptides have chain lengths of from 3 to 15 amino acids.

6. The compound according to claim 1, wherein the oligopeptides are chosen from the group consisting of homopolymers, copolymers or block copolymers.

7. The compound according to claim 1, wherein the polyethylene glycols have molar masses of at least 250 g/mol.

8. The compound according to claim 1, wherein C is a group chosen from the group consisting of thiazolidine, pyrrolidine and cyanopyrrolidine.

9. A pharmaceutical composition comprising the compound according to claim 1, optionally in combination with pharmaceutically acceptable carriers or adjuvants.

10. A cosmetic composition comprising the compound according to claim 1, optionally in combination with cosmetically acceptable carriers or adjuvants.

11. A pharmaceutical composition comprising at least one dipeptidyl peptidase IV (DP-IV) inhibitor compound of the general formula wherein A is an amino acid having at least one functional group in the side chain, B is a chemical compound covalently bound to at least one functional group in the side chain of A, chosen from the group consisting of:
(a) oligopeptides having a chain length of up to 20 amino acids, except for homopolymers of glycine consisting of up to 6 glycine monomers, and
(b) polyethylene glycols having molar masses of up to 20,000 g/mol, C is a group, amide-bonded to A, chosen from the group consisting of thiazolidine, pyrrolidine, cyanopyrrolidine, hydroxyproline, dehydroproline and piperidine, and at least one pharmaceutically acceptable carrier.

12. The pharmaceutical composition according to claim 11, wherein A is an α-amino acid.

13. The pharmaceutical composition according to claim 12, wherein A is a natural α-amino acid.

14. The pharmaceutical composition according to claim 13, wherein the amino acid is chosen from the group consisting of threonine, tyrosine, serine, arginine, lysine, aspartic acid, glutamic acid and cysteine.

15. The pharmaceutical composition according to claim 11, wherein the oligopeptides have chain lengths of from 3 to 15 amino acids.

16. The pharmaceutical composition according to claim 11, wherein the oligopeptides are chosen from the group consisting of homopolymers, copolymers and block copolymers.

17. The pharmaceutical composition according to claim 11, wherein the polyethylene glycols have molar masses of at least 250 g/mol.

18. The pharmaceutical composition according to claim 11, wherein C is a group chosen from the group consisting of thiazolidine, pyrrolidine and cyanopyrrolidine.

19. The pharmaceutical composition according to claim 11, further comprising pharmaceutically acceptable carriers.

* * * * *